United States Patent [19]

Noguchi et al.

[11] Patent Number: 4,956,019

[45] Date of Patent: Sep. 11, 1990

[54] NOVEL FLAKY COLOR PIGMENT AND PROCESS FOR PRODUCING THE SAME

[75] Inventors: Tamio Noguchi, Iwaki; Takaji Watanabe, Omiya, both of Japan

[73] Assignee: Merck Patent Gesellschaft Mit Beschrankter Haftung, Darmstadt, Fed. Rep. of Germany

[21] Appl. No.: 84,945

[22] Filed: Aug. 13, 1987

[30] Foreign Application Priority Data

Aug. 13, 1986 [JP] Japan ................................. 61-188614

[51] Int. Cl.$^5$ ............................ C09C 3/06; C09C 1/04
[52] U.S. Cl. ...................................... 106/415; 106/416; 106/417; 106/418; 106/425; 106/459
[58] Field of Search ..................... 106/309, 308 B, 296, 106/291, 417, 415, 425, 459, 416, 418

[56] References Cited

U.S. PATENT DOCUMENTS 3,650,793  3/1972  Goodspeed et al. ............ 106/308 B
4,435,220  3/1984  Watanabe et al. ................. 106/291
4,755,229  7/1988  Armanini ........................... 106/413

FOREIGN PATENT DOCUMENTS 58-21455  2/1983  Japan.

Primary Examiner—Paul Lieberman
Assistant Examiner—Christine A. Skane
Attorney, Agent, or Firm—Millen, White & Zelano

[57] ABSTRACT

Flaky colored pigment comprising fine flaky powder as base material, and zinc oxide and an inorganic color pigment attached to the surface thereof.

14 Claims, No Drawings

NOVEL FLAKY COLOR PIGMENT AND PROCESS FOR PRODUCING THE SAME

Summary of the Invention

This invention relates to novel, flaky colored pigments and to processes for producing the same. It is an object of the invention to provide novel, flaky colored pigments comprising fine flaky powder as base material, and zinc oxide and an inorganic color pigment attached to the surface thereof.

Upon further study of the specification and appended claims, further objects and advantages of this invention will become apparent to those skilled in the art.

These objects have been satisfied by producing novel, flaky color pigments comprising fine flaky powder and zinc oxide and an inorganic color pigment attached to the surface thereof. The objects have further been satisfied by provision of processes for production of such pigments as detailed below.

Detailed Description

The flaky colored pigments of this invention show unique color tone not to be expected with conventional zinc oxide pigment or calamine, exhibit pearlescent gloss, are free from color segregation when used in, for example, lotions, and have fine particles of zinc oxide capable of absorbing ultraviolet rays attached to the surface thereof. With these outstanding characteristics, the flaky pigments of this invention are suitable as an ingredient of cosmetics, such as lotion and cream; particularly when used in place of calamine in conventional calamine lotions, they exhibit unusual effects (unique color tone with no trouble of color segregation).

The flaky colored pigment of this invention is a type of pigment using fine flaky powder as base material. Typical examples of this base material include muscovite, phlogopite, sericite, talc, kaolin and barium sulfate. Besides these, fine flaky particles with an inorganic colored pigment attached thereto, for example, mica-titanium oxide and micairon complexes, may also be used as the base material. The particle size of this base material is 1 to 200 $\mu$m, preferably 3 to 70 $\mu$m. The amount of zinc oxide in the finished pigment is preferably about 5 to 70% based on the total weight of the flaky color pigment.

The flaky colored pigment of this invention may be produced from this base material in various ways. Typical methods provided by this invention are as described below.

(A) A process which comprises suspending fine flaky powder in water; treating the suspension with (a) an aqueous solution of zinc salt of an organic or inorganic acid and (b) an aqueous solution of an alkali metal or ammonium hydroxide, carbonate or bicarbonate, or urea, so as to deposit zinc hydroxide or basic zinc carbonate on the surface of said fine flaky powder, further treating the powder with fine particles of an inorganic pigment so as to deposit it on the surface of said fine flaky powder; and collecting the resulting solid by filtration, followed by washing with water, drying and calcination.

(B) A process which comprises suspending fine flaky powder in water; treating the suspension with (a) an aqueous solution of zinc salt of an organic or inorganic acid and (b) an aqueous solution of an alkali metal or ammonium hydroxide, carbonate or bicarbonate, or urea, so as to deposit zinc hydroxide or basic zinc carbonate on the surface of said fine flaky powder; collecting the resulting solid by filtration, followed by washing with water, drying and calcination; suspending the calcined powder thus obtained in water; and treating the suspended powder with fine particles of an inorganic color pigment so as to deposit it on the surface of said fine flaky powder.

(C) A process which comprises suspending, in water, flaky pigment composed of fine flaky powder and fine particles of an inorganic pigment deposited on the surface thereof; treating the suspension with (a) an aqueous solution of zinc salt of an organic or inorganic acid and (b) an aqueous solution of an alkali metal or ammonium hydroxide, carbonate or bicarbonate, or urea, so as to deposit zinc hydroxide or basic zinc carbonate on the surface of said fine flaky powder; and collecting the resulting solid by filtration, followed by washing with water, drying and calcination.

Each of the processes (A) to (C) is explained below in more detail.

(1) In general operation of process (A), the fine flaky powder is suspended in 100 parts of water, the suspension was stirred at 0° to 100°60 C., preferably at 20° to 80° C., and 5 to 45 wt% aqueous solution of zinc salt of an organic or inorganic acid is added while controlling the pH within the range from 7.0 to 9.5 by using 5 to 45 wt% aqueous solution an alkali metal or ammonium hydroxide, carbonate or bicarbonate, thereby depositing zinc hydroxide or basic zinc carbonate on the surface of said fine flaky powder. To the suspension thus obtained, is added with stirring an aqueous suspension of inorganic pigment prepared, for example, by suspending, in about 0.5 to 20 parts of water, 10 parts of the fine flaky powder used above and about 0.05 to 2 parts of an inorganic pigment (e.g., red iron oxide, cobalt blue and ultramarine blue) finely pulverized by a sand mill or the like. The resulting solid is collected by filtration, washed with water, dried, and calcined at a temperature higher than 500° C.

(2) Process (B) is a method suitable when using an inorganic pigment that is rather poor in thermal resistance, such as Prussian blue and yellow iron oxide. Zinc hydroxide or basic zinc carbonate is deposited on the surface of fine flaky powder in the same way as in process (A). After that, the solid matters are collected by filtration, washed with water, dried and calcined at a temperature higher than 500° C. The pigment thus obtained (about 10 parts) is then suspended in water (100 parts). To this suspension is added with stirring an aqueous suspension of inorganic pigment prepared by suspending, in about 0.5 to 20 parts of water, about 0.05 to 2 parts of an inorganic pigment (e.g., red iron oxide, cobalt blue and ultramarine blue) finely pulverized by a sand mill or the like. The resulting solid is collected by filtration, washed with water, and dried.

(3) In general operation of process (C), about 10 parts of flaky pigment, composed of fine flaky powder as base material and fine, inorganic colored pigment deposited on the surface thereof, is suspended in 100 parts water, and this suspension is treated in the same manner as in process (A) to deposit zinc hydroxide or basic zinc carbonate. The resulting solid is collected by filtration, washed with water, dried and calcined at a temperature higher than 500° C.

The above-mentioned aqueous solution of zinc salt of an organic or inorganic acid may also contain a titanium salt, such as titanium oxytitanate and titanium tetrachloride. Pigment with brighter gloss can be obtained by addition of such a titanium salt.

Typical examples of the zinc salt (a) mentioned above include zinc sulfate, chloride, nitrate, oxalate and tartrate. Sodium hydroxide, potassium hydroxide, ammonium hydroxide, sodium bicarbonate, potassium bicarbonate, ammonium bicarbonate, sodium carbonate, potassium carbonate and ammonium carbonate may be mentioned as examples of the alkali metal or ammonium hydroxide, carbonate or bicarbonate (b) mentioned above. Use of urea, which undergoes hot hydrolysis to form ammonia and carbon dioxide, gives the same result as when ammonium hydroxide or carbonate is used.

Illustrative examples of the inorganic pigment include iron cobalt (e.g., red, yellow and black iron oxides), cobalt oxide pigment (e.g., cobalt blue, cobalt green and cobalt violet), ultramarine blue, Prussian blue and manganese violet.

In all of the pigments preparable in accordance with this invention, the relative amounts of the components can be within the following weight percentage ranges: zinc oxide 5-70%, inorganic color pigment 0.5-20%, all based on the total weight of the final pigment, the remainder, of course, being the substrate.

Except as noted, all details of the production of the pigment of the invention are conventional.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

Example 1

Muscovite about 1 to 15 microns in diameter ( 300 g ) was suspended in 3000 ml water, the suspension was heated to 80° C., and a solution of 50 g titanyl sulfate ( $TiOSO_4 \cdot 2H_2O$ ) and 2 g conc. sulfuric acid in 330 ml water was added to the suspension over a period of 30 minutes, while maintaining the pH within the range from 1.8 to 2.2 by addition of 15 wt% aqueous solution of ammonium carbonate. The pH was raised to 5.0 to 6.0 by adding 15 wt% aqueous solution of ammonium carbonate, 500 g of 28 wt% aqueous solution of zinc nitrate was added over a period of two hours while maintaining the pH within the range from 5.0 to 8.0 by addition of 15 wt% aqueous solution of ammonium carbonate.

To the resulting suspension was added with stirring 4 g of red iron oxide finely pulverized by a sand mill, and the precipitate which separated out was collected by filtration, washed with water to remove soluble salts, dried at about 105° to 110° C., and calcined at 650° to 670° C. for one hour.

The pink pigment thus obtained was found to have titanium oxide, zinc oxide and iron oxide pigment deposited on the surface of muscovite.

Example 2

Muscovite about 5 to 20 microns in diameter ( 300 g ) was suspended in 3000 ml of water, the suspension was heated to 80° C., and a solution of 50 g titanyl sulfate ( $TiOSO_4 \cdot 2H_2O$ ) and 2 g conc. sulfuric acid in 330 ml water was added to the suspension over a period of 30 minutes, while maintaining the pH within the range from 1.8 to 2 2 by addition of 15 wt% aqueous solution of potassium carbonate. The pH was raised to 5.0 to 6.0 by adding 15 wt% aqueous solution of potassium carbonate, and 500 g of 20 wt% aqueous solution of zinc chloride was added over a period of two hours while maintaining the pH within the range from 5.0 to 8.0 by addition of 15 wt% aqueous solution of potassium carbonate.

To this suspension was added with stirring 4 g of red iron oxide finely pulverized by a sand mill, and the precipitate which separated out was collected by filtration, washed with water to remove soluble salts, dried at about 105° to 110° C., and calcined at 650° to 670° C. for one hour.

The pink pigment thus obtained was found to have titanium oxide, zinc oxide and iron oxide pigment deposited on the surface of muscovite.

Example 3

Muscovite about 1 to 15 microns in diameter ( 300 g ) was suspended in 3000 ml of water, the suspension was heated to 80° C., and a solution of 50 g titanyl sulfate ( $TiOSO_4 \cdot 2H_2O$ ) and 2 g conc. sulfuric acid in 330 ml water was added to the suspension over a period of 30 minutes with stirring, while maintaining the pH within the range from 1.8 to 2.2 by addition of a 1:1 mixture of 15 wt% aqueous solution of potassium carbonate and 15 wt% aqueous solution of potassium bicarbonate. The pH was raised to 5.0 to 6.0 by adding the same mixture of alkaline solution as above, and 500 g of 28 wt% aqueous solution of zinc nitrate was added over a period of two hours while maintaining the pH within the range from 5.0 to 6.0 by addition of the same mixture of alkaline solutions as above.

To this suspension was added with stirring 4 g of red iron oxide finely pulverized by a sand mill, and the precipitate which separated out was collected by filtration, washed with water to remove soluble salts, dried at about 105° to 110° C., and calcined at 650° to 670° C. for one hour.

The pink pigment thus obtained was found to have titanium oxide, zinc oxide and iron oxide pigment deposited on the surface of muscovite.

Example 4

Muscovite about 1 to 15 microns in diameter ( 300 g ) was suspended in 3000 ml water, 300 g of urea and a solution of 100 g zinc nitrate, 30 g titanyl sulfate ( $TiOSO_4 \cdot 2H_2O$ ) and 2 g conc. sulfuric acid in 300 ml water were added to this suspension over a period of 30 minutes, and the mixture was heated at 90° to 98° C. for 4.5 hours with stirring.

After the pH was raised to 7.5 to 9.5 by adding 15 wt% aqueous solution of sodium carbonate, 4 g of red iron oxide finely pulverized by a sand mill was added with stirring, and the precipitate which separated out was collected by filtration, washed with water to remove soluble salts, dried at about 105° to 110° C., and calcined at 650°60 to 670° C. for one hour.

The pink pigment thus obtained was found to have titanium oxide, zinc oxide and iron oxide pigment deposited on the surface of muscovite.

Example 5

Muscovite about 5 to 20 microns in diameter (100 g) was suspended in 1000 ml water, the suspension was heated to 80° C., and 300 g of 25 wt% aqueous solution of zinc nitrate containing 1 g conc. nitric acid was added to this suspension over a period of two hours with stirring, while maintaining the pH within the range from 7.0 to 8.5 by addition of 20 wt% aqueous solution of potassium carbonate. To the resulting suspension was added 10 g of aqueous suspension of 4 g red iron oxide finely pulverized by a sand mill. The precipitate which separated out was collected by filtration, washed with water to remove soluble salts, dried at about 105° to 110° C., and calcined at 650° to 670°60 C. for one hour.

The pink pigment thus obtained was found to have zinc oxide and iron oxide pigment deposited on the surface of muscovite.

Example 6

Pink pigment was produced in the same manner as in Example 5 except that talc about 1 to 20 microns in diameter was used in place of muscovite.

Example 7

Muscovite about 5 to 20 microns in diameter (300 g) was suspended in 3000 ml water, the suspension was heated to 80° C., and 330 ml of an aqueous solution containing 50 g titanyl sulfate ($TiOSO_4 \cdot 2H_2O$) and 2 g conc. sulfuric acid was added to the suspension over a period of 30 minutes with stirring, while maintaining the pH within the range from 1.8 to 2.2 by addition of 15 wt%-aqueous solution of potassium carbonate. After the pH was raised to 5.0 to 6.0 by adding 15 wt% aqueous solution of potassium carbonate, 500 g of 28 wt% aqueous solution of zinc nitrate containing 1 g conc. nitric acid was added over a period of two hours while maintaining the pH within the range from 7.0 to 8.5 by addition of 15 wt% aqueous solution of potassium carbonate.

To this suspension was added with stirring 5 g of cobalt blue (CoB) finely pulverized by a sand mill, and the precipitate which separated out was collected by filtration, washed with water to remove soluble salts, dried at about 105° to 110° C., and calcined at 650° to 670° C. for one hour.

The whitish-blue pigment thus obtained was found to have zinc oxide and cobalt blue deposited on the surface of mica-titanium oxide base material.

Example 8

Mica/titanium oxide complex assuming blue interference color (150 g), prepared by coating muscovite about 10 to 60 microns in diameter with about 50 wt% of titanium oxide, was suspended in 1.5 liters of water, the suspension was heated to 80° C., and 250 g of 42 wt% aqueous solution of zinc nitrate was added to this suspension over a period of 80 minutes with stirring, while maintaining the pH within the range from 8.0 to 9.0 by addition of 30 wt% aqueous solution of potassium carbonate. The solid was collected by filtration, washed with water to remove soluble salts, dried at about 105° to 110° C. for 18 hours, and calcined at 650° C. for one hour.

The pigment assuming blue interference color thus obtained was found to have fine powder of zinc oxide deposited on the surface of muscovite/titanium oxide base material.

Example 9

Reddish brown, mica/iron oxide complex (50 g), prepared by coating muscovite about 10 to 60 microns in diameter with about 45 wt% of iron titanium oxide, was suspended in 700 ml of water, the suspension was heated to 80° C., and 80 g of 28 wt% aqueous solution of zinc nitrate was added to this suspension over a period of 80 minutes with stirring, while maintaining the pH within the range from 8.0 to 9.0 by addition of 30 wt% aqueous solution of potassium carbonate. The solid was collected by filtration, washed with water to remove soluble salts, dried at about 105° to 110° C. for 18 hours, and calcined at 650° C. for one hour.

The light reddish-brown pigment thus obtained was found to have fine powder of zinc oxide deposited on the surface of muscovite/iron oxide base material.

Example 10

Silver-colored mica/titanium oxide complex (300 g), prepared by coating muscovite about 5 to 20 microns in diameter with about 35 wt% of titanium oxide, was suspended in 3 liters of water, the suspension was heated to 80° C., and 500 g of 42 wt% aqueous solution of zinc nitrate was added to this suspension over a period of 80 minutes with stirring, while maintaining the pH within the range from 8.0 to 9.0 by addition of 30 wt% aqueous solution of potassium carbonate.

To the resulting suspension was added with stirring a suspension of 36 g silica-treated ultramarine blue finely pulverized with a sand mill in 150 ml of water, and the solid was collected by filtration, washed with water to remove soluble salts, dried at about 105° to 110° C., and calcined at 650° C. for one hour under a nitrogen stream.

The light blue, glossy pigment thus obtained was found to have zinc oxide and ultramarine blue deposited on the surface of muscovite/titanium oxide.

It was confirmed by electron-microscopic observation that the pigment obtained in the Examples described above consists of fine flaky powder, and fine particles of zinc oxide and inorganic color pigment attached to the surface thereof.

It was also ascertained that the novel, flaky colored pigment thus prepared, when used in cosmetics (especially in lotions), is better than conventional zinc oxide pigment and calamine, particularly in gloss, brightness, as well as in spreadability on, and adhesion to, the skin.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A flaky colored pigment comprising a flaky powder substrate with a layer of zinc oxide on the substrate surface and on said zinc oxide layer an inorganic colored pigment layer or comprising a flaky powder substrate with an inorganic colored pigment layer on the substrate surface and on said inorganic colored pigment layer a zinc oxide layer, in each case said inorganic colored pigment layer being deposited from a suspension of said inorganic colored pigment which has been added to said suspension in the form of already-formed pigment particles.

2. A pigment according to claim 1, wherein the substrate is muscovite, phlogopite, sericite, talc, kaolin or barium sulfate.

3. A pigment according to claim 1, wherein the substrate is a mica-titanium oxide or mica-iron oxide complex.

4. A pigment according to claim 1 wherein the particle size of the substrate is about 1–200 μm.

5. A pigment according to claim 1, wherein the particle size is about 3–70 μm.

6. A pigment according to claim 1, wherein the inorganic colored pigment is iron oxide, cobalt oxide, ultramarine blue, Prussian blue or manganese violet.

7. A pigment according to claim 6, wherein the iron oxide is a red, yellow, or black iron oxide.

8. A pigment according to claim 6, wherein the cobalt oxide is cobalt blue, cobalt green or cobalt violet.

9. A pigment according to claim 1, wherein the amount of zinc oxide is 5–70% b weight based on the total weight of the flaky colored pigment.

10. A pigment according to claim 1, wherein the amount of inorganic colored pigment is 0.5–20% by weight based on the total weight of the flaky colored pigment.

11. A pigment according to claim 1, comprising a flaky powder substrate with an inorganic colored pigment in the substrate surface and zinc oxide therein.

12. A flaky colored pigment prepared by a process comprising suspending a flaky powder substrate in water; treating the suspension with (a) an aqueous solution of zinc salt of an organic or inorganic acid and (b) an aqueous solution of an alkali metal or ammonium hydroxide, carbonate or bicarbonate, or urea, so as to deposit zinc hydroxide or basic carbonate on the surface of said flaky powder substrate; further treating the powder with fine particles of an inorganic pigment so as to deposit said pigment on the surface of said flaky powder substrate; collecting the resulting solid by filtration, washing with water, drying and calcining the solid.

13. A flaky colored pigment prepared by a process comprising suspending a flaky powder substrate in water; treating the suspension with (a) an aqueous solution of zinc salt of an organic or inorganic acid and (b) an aqueous solution of an alkali metal or ammonium hydroxide, carbonate or bicarbonate, or urea, so as to deposit zinc hydroxide or basic zinc carbonate on the surface of said flaky powder substrate; collecting the resulting solid by filtration, washing with water, drying and calcining the solid; suspending the calcined solid thus obtained in water; and treating the suspended solid with particles of an inorganic color pigment so as to deposit it on the surface of said flaky powder substrate.

14. A flaky colored pigment prepared by a process comprising suspending, in water, a flaky pigment composed of a flaky powder substrate and fine particles of an inorganic pigment deposited on the surface thereof; treating the suspension with (a) an aqueous solution of zinc salt of an organic or inorganic acid and (b) an aqueous solution of an alkali metal or ammonium hydroxide, carbonate or bicarbonate, or urea, so as to deposit zinc hydroxide or basic zinc carbonate on the surface of said flaky powder substrate; collecting the resulting solid by filtration; washing with water, drying and calcining the solid.

* * * * *